US011049605B1

(12) United States Patent
Peters

(10) Patent No.: US 11,049,605 B1
(45) Date of Patent: Jun. 29, 2021

(54) COMPUTER-IMPLEMENTED SYSTEMS AND METHODS FOR GENERATING TAILORED MEDICAL RECIPES FOR MENTAL HEALTH DISORDERS

(71) Applicant: Cortery AB, Domsten (SE)

(72) Inventor: Filip Ludwig Peters, Domsten (SE)

(73) Assignee: Cortery AB, Domstein (SE)

( * ) Notice: Subject to any disclaimer, the term of this patent is extended or adjusted under 35 U.S.C. 154(b) by 0 days.

(21) Appl. No.: 16/946,679

(22) Filed: Jun. 30, 2020

(51) Int. Cl.
| | |
|---|---|
| *G16H 10/60* | (2018.01) |
| *G16H 15/00* | (2018.01) |
| *G16H 20/70* | (2018.01) |
| *G16H 10/20* | (2018.01) |
| *G16H 50/20* | (2018.01) |
| *G16H 40/67* | (2018.01) |
| *G16H 40/63* | (2018.01) |
| *A61B 10/00* | (2006.01) |
| *A61B 5/00* | (2006.01) |
| *A61B 5/024* | (2006.01) |
| *G06N 3/02* | (2006.01) |

(52) U.S. Cl.
CPC ............ *G16H 20/70* (2018.01); *A61B 5/024* (2013.01); *A61B 5/4088* (2013.01); *A61B 5/4836* (2013.01); *A61B 5/749* (2013.01); *A61B 10/0051* (2013.01); *G06N 3/02* (2013.01); *G16H 10/20* (2018.01); *G16H 40/63* (2018.01); *G16H 40/67* (2018.01); *G16H 50/20* (2018.01)

(58) Field of Classification Search
CPC ........ G16H 10/40; G16H 10/60; G16H 10/20; G16H 20/40; G16H 70/20; G16H 40/67; G16H 80/00; G16H 50/20; G16H 50/50; G16H 20/10; G16H 20/00; G16H 50/70; G16H 20/70; G16H 50/30; G16H 40/20; G16H 70/00; G16H 15/00; G16H 20/30; G16H 20/60; G16H 30/20; G06Q 10/10; G06Q 10/101; G06Q 50/24; A61B 5/0002; G06F 19/3418; G16B 20/00; G16B 40/00; G16B 25/00
See application file for complete search history.

(56) References Cited

U.S. PATENT DOCUMENTS

| | | | | |
|---|---|---|---|---|
| 2017/0098053 | A1* | 4/2017 | Pandey | G16H 10/60 |
| 2018/0361731 | A1* | 12/2018 | Kameshima | B41J 2/0057 |

(Continued)

*Primary Examiner* — Maroun P Kanaan
(74) *Attorney, Agent, or Firm* — Brett A. Schenck

(57) ABSTRACT

Computer-implemented systems and methods for generating tailored medical recipes for mental health disorders. The systems include a processor, a memory, and a server. The memory is configured to register a user over a communication application through a registration module; receive demographic data through a demography module; receive voice data of the user through a voice module; receive bio-sample data of the user through a bio-sample module; receive face image data of the user through a camera module; receive mental health questionnaire data from the user through a questionnaire module; and transmit a final dataset through a data transmission module. The server is configured to process the final dataset received from the data transmission module by applying a machine learning module; generate the tailored medical recipes; and transmit the tailored medical recipes to one or more computing devices of the user over the network.

24 Claims, 9 Drawing Sheets

(56) References Cited

U.S. PATENT DOCUMENTS

| | | | |
|---|---|---|---|
| 2020/0038412 A1* | 2/2020 | Barbut | A61K 9/0043 |
| 2020/0121236 A1* | 4/2020 | Gao | G16H 20/10 |
| 2020/0176098 A1* | 6/2020 | Lucas | G16H 15/00 |

* cited by examiner

COMPUTER-IMPLEMENTED SYSTEMS AND METHODS FOR GENERATING TAILORED MEDICAL RECIPES FOR MENTAL HEALTH DISORDERS

CROSS-REFERENCES TO RELATED PATENT APPLICATIONS

Not Applicable.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISK APPENDIX

Not Applicable.

BACKGROUND

Technical Field

The inventive subject matter presented herein is generally directed towards computer-implemented systems and methods for assessing mental health for providing tailored medical recipes. More particularly it is directed to, but not limited to, computer-implemented systems and methods for generating tailored medical recipes for mental health disorders including, but not limited to, anxiety and/or depression by applying machine learning.

Description of the Related Art

Artificial intelligence (AI) and machine learning (ML) has the potential to save the lives of current and future patients and is something that is starting to be seen across healthcare services across the world. With ever-larger computational powers, understanding of the possibilities of machine learning, and the growth of mobile technology in society, the ability to cost-efficiently collect patient data and provide personalized healthcare has reached an important point. Insights into the complex interplay between how lifestyle, genetics, biochemical reactions such as gut microbiomes, are affecting our mental health are becoming more and more apparent. Many of the aforementioned factors may have been partially overlooked in the existing approach to improve mental health. With mental health disorders growing and with the antidepressant market growing into the double digits, new approaches to mental health medicines are needed. Worryingly, rates of depression and anxiety in younger cohorts of society are growing at even higher levels.

Typically, clinical mental health interactions between clinicians and patients may be prone to bias and there may be social stigma related to a mental health disorder. While common antidepressants such as Selective Serotonin Reuptake Inhibitors (SSRIs) are commonly prescribed, there is some evidence pointing towards commonly prescribed antidepressants being possibly addictive in the long run. It is known that existing antidepressants may be ineffective in as many as 60% of patients. Additionally, several natural health medicines and remedies have been shown to be equal to several prescription-based medical anti-depressants. Several meta-studies have demonstrated that such remedies may have minimal side-effects and are typically considered safe to take. Such natural health remedies may include but are not limited to St. John's Wort, omega-3 fatty acids, chamomile, SAMe, saffron, 5-HTP, DHEA, folate and zinc.

Further, existing conventional personalized medicine can be based on DNA and genome sequencing and these techniques are beginning to be viewed under increased scrutiny. As is well known, such data may not be truly anonymous and, if it fell into the wrong hands, it could become a severe breach of patient data privacy not only for the patients themselves but also for persons sharing familiar traits and similarities based on the results of the DNA and genome sequencing that could be traced back to related family members.

Personalized medicines are sometimes recommended based on one more bio-sample collected from a patient. A number of bio-sample collection methods exist that require tedious methods of collection and a long waiting times for each analysis to be completed. Other issues include the quality of the samples which can be affected by exposure to differing environments including exposure during transportation from clinical settings to laboratories. The extended waiting times needed to receive the results and the resulting mental health disorder treatment recommendations and protocols adds to the cost and time to both patients and society.

Therefore, there is a need for computer-implemented systems and methods for generating one or more tailored medical recipes to aid in the treatment of mental health disorders that leverage machine learning tools to create affordable and time sensitive personalized healthcare. Further, there is a need for a computer-implemented system and method for providing an online healthcare platform that promotes healthcare inclusivity for younger generations that are increasingly used to consuming through online sources. Furthermore, there is a need for a computer-implemented system and method for adhering to a precautionary principle about the long-term effects of current mental health disorder medicines that are being actively used in society.

Thus, in view of the above, there is a long-felt need in the healthcare industry to address the aforementioned deficiencies and inadequacies.

SUMMARY

Computer-implemented systems and methods for generating tailored medical recipes for mental health disorders are provided, as shown in and/or described in connection with at least one of the figures.

One aspect of the present disclosure relates to a computer-implemented method for generating tailored medical recipes for mental health disorders. The computer-implemented method includes a step of registering a user over a communication application by receiving one or more credentials from the user for providing access to the communication application through a registration module. The computer-implemented method includes a step of receiving demographic data pertaining to the user through a demography module. The computer-implemented method includes a step of receiving voice data of the user through a voice module. The computer-implemented method includes a step of receiving bio-sample data of the user through a bio-sample module. The computer-implemented method includes a step of receiving face image data of the user through a camera module. The computer-implemented method includes a step of receiving mental health questionnaire data from the user through a questionnaire module. The computer-implemented method includes a step of transmitting a final dataset by compiling the demographic data, the voice data, the bio-sample data, the face image data, and the mental health questionnaire data of the user through a data transmission module. The computer-implemented method includes a step of processing the final dataset received from the data transmission module over a network by applying a machine learning module. The computer-implemented method includes a step of generating the tailored medical recipes based on the final dataset processed by the machine learning module. The computer-implemented method includes a step of transmitting the tailored medical recipes to one or more computing devices of the user.

In an embodiment, the bio-sample module is configured to facilitate the user to collect a bio-sample from salivary glands in a form of saliva.

In an embodiment, the bio-sample module is configured to facilitate the user to place the bio-sample on a reactant paper comprising a plurality of reactant properties pertaining to chemical information of the user's body.

In an embodiment, the bio-sample module is configured to facilitate the user to capture an image of the reactant paper upon placing the bio-sample to obtain the bio-sample data.

In an embodiment, the communication application is executable on the computing devices of the user and implemented on one or more operating systems.

In an embodiment, the questionnaire module presents one or more questions pertaining to the diagnosis of mental health disorders and a plurality of corresponding selectable answers.

In an embodiment, the questionnaire module facilitates the user to select at least one answer from the plurality of corresponding selectable answers to the one or more questions to obtain the mental health questionnaire data.

An aspect of the present disclosure relates to a computer-implemented system for generating tailored medical recipes for mental health disorders. The computer-implemented system includes a processor, a memory, and a server. The memory is communicatively coupled to the processor, wherein the memory stores instructions executed by the processor. The memory is configured to register a user over a communication application by receiving one or more credentials from the user for providing access to the communication application through a registration module; receive demographic data pertaining to the user through a demography module; receive voice data of the user through a voice module; receive bio-sample data of the user through a bio-sample module; receive face image data of the user through a camera module; receive mental health questionnaire data from the user through a questionnaire module; and transmit a final dataset by compiling the demographic data, the voice data, the bio-sample data, the face image data, and the mental health questionnaire data of the user through a data transmission module. The server is communicatively coupled to the memory over a network. The server is configured to process the final dataset received from the data transmission module by applying a machine learning module; generate the tailored medical recipes based on the final dataset processed by the machine learning module; and transmit the tailored medical recipes to one or more computing devices of the user over the network.

In an embodiment, the bio-sample module is configured to facilitate the user to collect a bio-sample from salivary glands in a form of saliva.

In an embodiment, the bio-sample module is configured to facilitate the user to place the bio-sample on a reactant paper comprising a plurality of reactant properties pertaining to chemical information of the user's body.

In an embodiment, the bio-sample module is configured to facilitate the user to capture an image of the reactant paper upon placing the bio-sample to obtain the bio-sample data.

In an embodiment, the communication application is executable on the computing devices of the user and implemented on one or more operating systems.

In an embodiment, the questionnaire module presents one or more questions pertaining to the diagnosis of mental health disorders and a plurality of corresponding selectable answers.

In some embodiments, the questionnaire module facilitates the user to select at least one answer from the plurality of corresponding selectable answers to the one or more questions to obtain the mental health questionnaire data.

Accordingly, one advantage of the present inventive subject matter is that it provides computer-implemented methods and systems for mental health assessment and personalized mental health medicine generation. Tailored medical recipes or personalized medicine for mental health disorders has the potential of being more accurate while at the same time leading to fewer side-effects.

Another advantage of the inventive subject matter is that embodiments provide computer-implemented methods and systems that incorporate reminders, nudges, and notifications into the communication application to help the user stick to their medicine which may enable the patient to be more inclined to adhere to their medication schedule and increase the efficacy of the medicine.

Another advantage of the inventive subject matter is that embodiments allow for an interactive process, without the need for the patient to take up resources of a healthcare system and allow for the patient to reach an ideal, personalized recipe in a shorter amount of time. The scientific community is becoming more aware of non-traditional interventional factors such as lifestyle playing an important factor in mental health as well as the impact of different types of microbiome levels in the gut on mental health disorder rates.

Another advantage of the inventive subject matter is that embodiments can provide an accurate assessment of the user's true mental health.

Another advantage of the inventive subject matter is that embodiments allow the utilization of a data-driven approach to provide robustness across patient cohorts in terms of objectivity and interpretability and may furthermore not be prone to environmental circumstances of clinical settings which may interfere with the communicative process between a clinician and a patient.

Another advantage of the inventive subject matter is that embodiments allow for the incorporation of safe natural health medicines into a personalized mental health treatment plan in order to provide safe medicine to patients in a shorter amount of time.

Another advantage of the inventive subject matter is that embodiments employ machine-learning enabled image analysis to analyze one or more bio-samples which can be beneficial for example because the sample does not need to be transported far distances to a lab for analysis which may lead to increased integrity of the bio-sample as there would be less opportunity for the sample to be interfered with and as well as to interact with different undesirable environments.

Yet another advantage of the inventive subject matter is that embodiments can expedite the overall process of getting personalized medicine, for instance they can lessen the time that is taken from when the bio-sample is collected to when the data bio-sample can be analyzed.

Yet another advantage of the inventive subject matter is that embodiments can reduce the time to predict potential symptom reducing medicines to reduce the prevalence of adverse events resulting from mental health disorders.

Yet another advantage of the inventive subject matter is that the risk of date loss or leakage may be reduced. Typically, the microbiome is correlated with depression. The microbiome can furthermore be found in bio-samples. Therefore, salivary bio-samples should have some correlation to rates of mental health. The bio-sample collection process of the inventive subject matter does not aim to sequence DNA or genome as may typically be common, but strictly identifies characteristics pertaining to mental health, leading to data results that are much more unique and subject to higher privacy concerns.

Currently, mental health disorders are particularly growing amongst younger generations. These younger generations may utilize embodiments of the present computer-implemented systems and methods for fulfilling their needs of mental health service in a way that integrates more seamlessly with their everyday technology use and habits.

These features and advantages of the present disclosure may be appreciated by reviewing the following description of the present specification along with the accompanying figures wherein like reference numerals refer to like elements.

BRIEF DESCRIPTION OF THE DRAWINGS

The accompanying drawings illustrate the embodiments of systems, methods, and other aspects of the disclosure. A person with ordinary skill in the art will appreciate that the illustrated element boundaries (e.g., boxes, groups of boxes, or other shapes) in the figures represent only exemplary boundaries. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope of the inventive subject matter, wherein similar designations denote similar elements, and in which.

DETAILED DESCRIPTION

The present description is best understood with reference to the detailed figures and detailed description set forth herein. Various embodiments of the present system and method have been discussed with reference to the figures. However, those skilled in the art will readily appreciate that the detailed description provided herein with respect to the figures are merely for explanatory purposes and the present systems and methods will extend beyond the described embodiments. For instance, the teachings presented herein as well as the needs of any particular application may yield multiple alternative and suitable approaches to implement the functionality of any detail of the present systems and methods described herein. Therefore, any approach to implement the present system and method may extend beyond certain implementation choices in the following embodiments.

According to the described embodiments, the methods of the inventive subject matter may be implemented by performing or completing manually, automatically, and/or any combination thereof. The term "method" refers to manners, means, techniques and procedures for accomplishing any task including, but not limited to, those manners, means, techniques, and procedures either known to the person skilled in the art or readily developed from existing manners, means, techniques and procedures by practitioners of the art to which the present inventive subject matter belongs. The persons skilled in the art will envision many other possible variations within the scope of the present system and method described herein.

Figure 1:
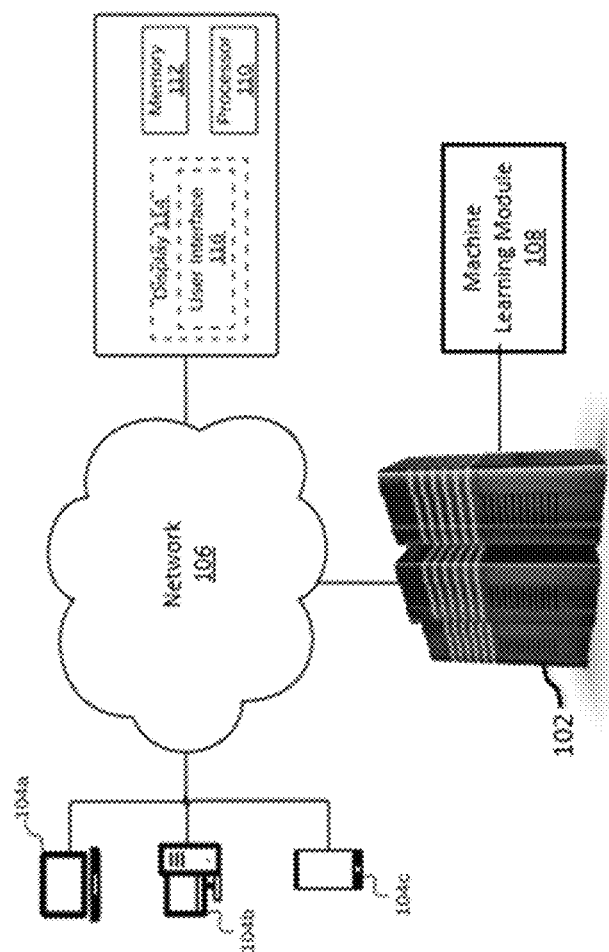
FIG. 1 illustrates a block diagram of the present system for generating one or more tailored medical recipes for mental health disorders in accordance at least one embodiment of the claimed subject matter.

FIG. 1 illustrates a block diagram of the present system 100 for generating one or more tailored medical recipes for mental health disorders, in accordance with embodiments of the inventive subject matter. In these embodiments, the computer-implemented system 100 includes a processor 110, a memory 112, and a server 102. The memory 112 is communicatively coupled to the processor 110, wherein the memory 112 stores instructions executed by the processor 110. The memory 112 may be a non-volatile memory or a volatile memory. Examples of non-volatile memory may include, but are not limited to flash memory, a Read Only Memory (ROM), a Programmable ROM (PROM), Erasable PROM (EPROM), and Electrically EPROM (EEPROM) memory. Examples of volatile memory may include but are not limited Dynamic Random-Access Memory (DRAM), and Static Random-Access memory (SRAM).

The processor 110 may include at least one data processor for executing program components for executing user- or system-generated requests. Processor 110 may include specialized processing units such as integrated system (bus) controllers, memory management control units, floating point units, graphics processing units, digital signal processing units, and the like.

Processor 110 may include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 110 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 110 may be disposed of in communication with one or more input/output (I/O) devices via an I/O interface. I/O interface may employ communication protocols/methods such as, without limitation, audio, analog, digital, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), and the like.

In many of the embodiments, the system 100 requires a user to register on a communication application configured within one or more computing devices 104 (for example, a laptop 104a, a desktop 104b, and a smartphone 104c). Other examples of the computing devices 104, may include but are not limited to a phablet and a tablet. A user may include a patient, a patient using the communication application using the computing devices 104 such as those included in the embodiments, or such a computing device itself. A user may also be an administrator or a remote user alone or in conjunction with another user or any combination of these. The processor 110, memory 112, server 102, and the computing devices 104 are communicatively coupled over a network 106. Network 106 may be a wired or a wireless network, and the examples may include but are not limited to the internet, Wireless Local Area Network (WLAN), Wi-Fi, Long Term Evolution (LTE), Worldwide Interoperability for Microwave Access (WiMAX), and General Packet Radio Service (GPRS).

Memory 112 further includes various modules that enable the present computer-implemented system 100 for generating one or more tailored medical recipes for mental health disorders. These modules are explained in detail in conjunction with FIG. 2. The present computer-implemented system 100 may further include a display 114 having a User Interface (UI) 116 that may be used by the user or an administrator to initiate a request to view the tailored medical recipes and provide various inputs to the present computer-implemented system 100. In an embodiment, the User Interface (UI or GUI) 116 is a convenient interface for accessing the information related to the tailored medical recipes, including the demographic data, the voice data, the bio-sample data, the face image data, and the mental health questionnaire data of the user. Display 114 may further be used to display tailored medical recipes to the users. The functionality of the computer-implemented system 100 may alternatively be configured within each of the plurality of computing devices 104.

Figure 2:
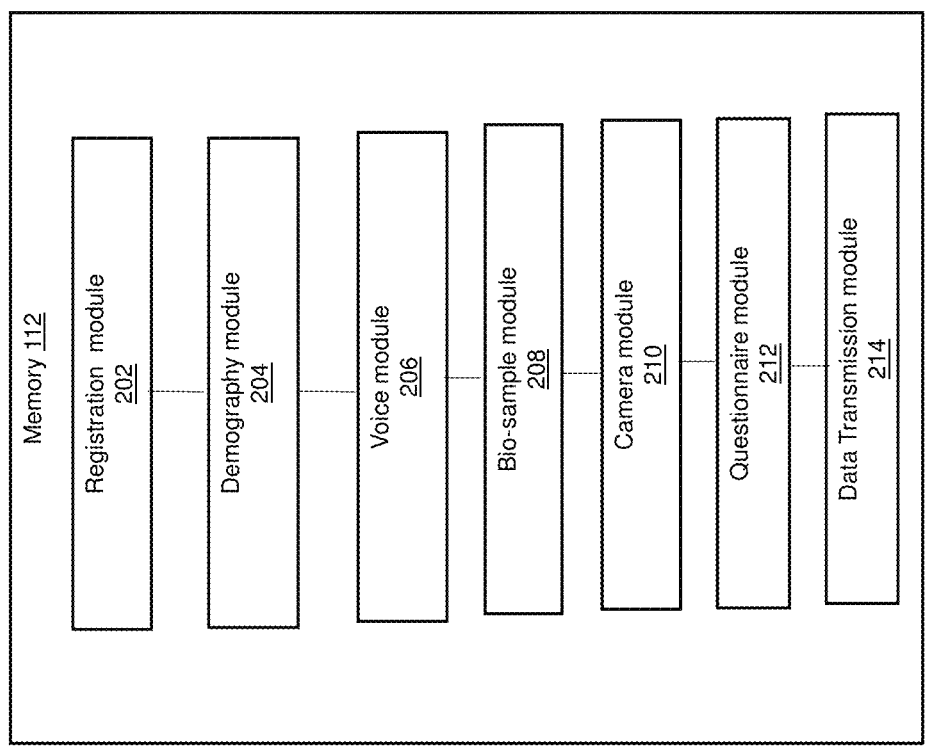
FIG. 2 illustrates a block diagram of the various modules within a memory of a computing device in accordance at least one embodiment of the claimed subject matter.

FIG. 2 illustrates a block diagram of the various modules within a memory 112 of a computing device 104, in accordance with embodiments of the inventive subject matter. FIG. 2 is explained in conjunction with FIG. 1. The memory 112 includes a registration module 202, a demography module 204, a voice module 206, a bio-sample module 208, a camera module 210, a questionnaire module 212, and a data transmission module 214. These modules are software components or part of a program that contains one or more routines.

The memory 112 is configured to register a user over a communication application by receiving one or more credentials from the user for providing access to the communication application through a registration module 202. Examples of the credentials including but not limited to a username, password, age, gender, phone number, email address, location, etc. In an embodiment, the communication application is executable on the computing devices 104 of the user and implemented on one or more operating systems such as Android®, iOS®, Windows®, etc. In some embodiments, the communication application is commercialized as a mental health monitoring application which is a software application, or a mobile application or a web application.

The memory 112 is configured to receive demographic data pertaining to the user through a demography module 204. In an embodiment, the user is prompted to enter his/her demographic data. Demographic data such as gender, ethnicity, weight, and height may be important in determining the efficacy of personalized medicine.

Figure 3:
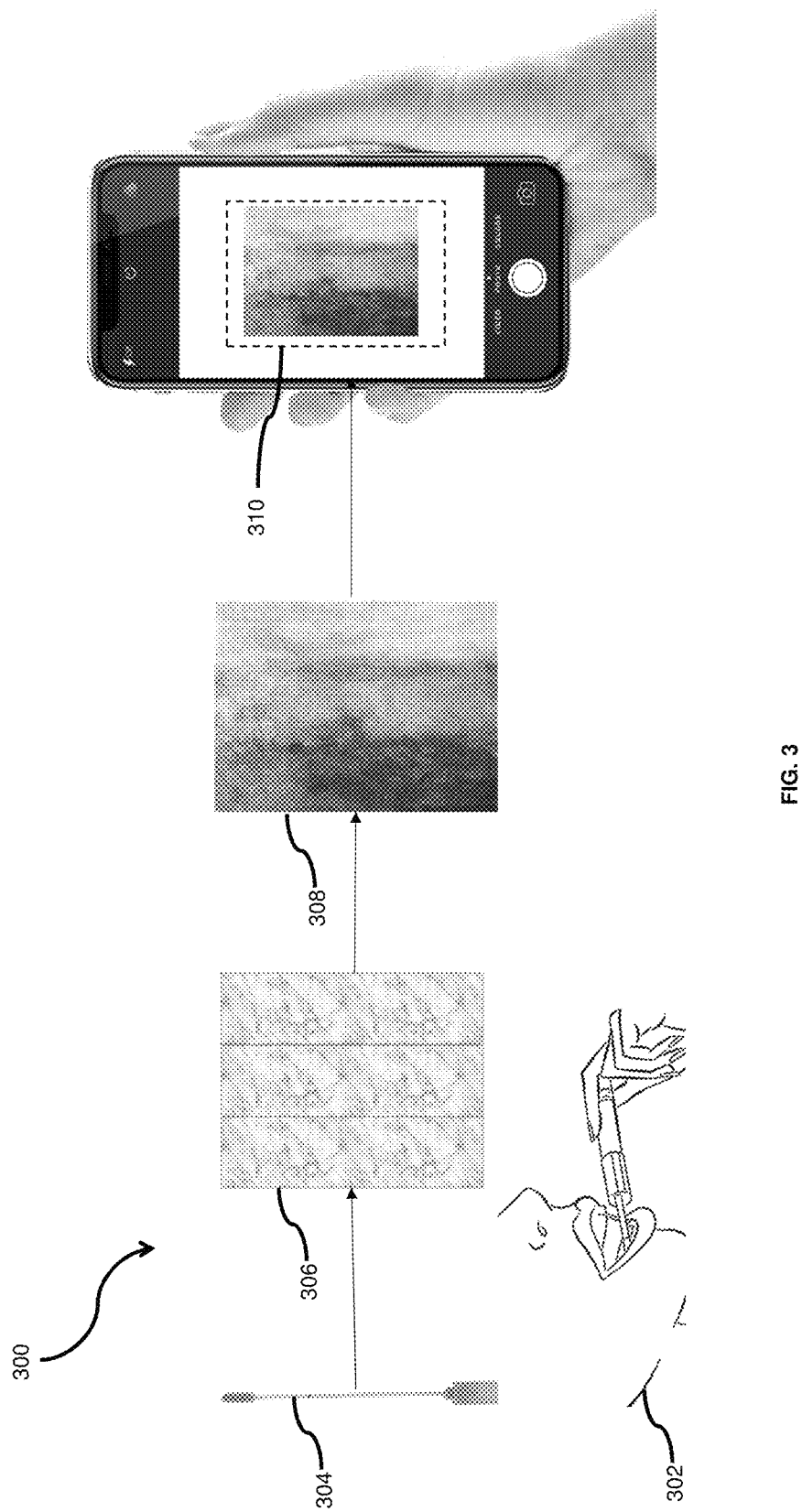
FIG. 3 illustrates a perspective view of receiving the bio-sample from a user in accordance at least one embodiment of the claimed subject matter.

The memory 112 is configured to receive bio-sample data of the user through a bio-sample module 208. FIG. 3 illustrates a perspective view of receiving the bio-sample from the user 302, in accordance with at least one embodiment. FIG. 3 is explained in conjunction with FIG. 2. The bio-sample module 208 is configured to facilitate user 302 to collect a bio-sample from salivary glands in a form of saliva by using a tool 304 such as a swab. The bio-sample module 208 is configured to facilitate the user to place the bio-sample on a reactant paper 306 comprising a plurality of reactant properties pertaining to chemical information of the user's body. The reactant paper 306 changes the color (308) upon receiving the bio-sample. In an embodiment, the bio-sample module 208 is configured to facilitate the user to capture an image 310 of the reactant paper 306 upon placing the bio-sample to obtain the bio-sample data.

According to embodiments of the inventive subject matter, a user is prompted to collect bio-sample from the salivary glands in the forms of saliva. The bio-sample may be placed on a reactant material. Different parts of the reactant paper may have different reactant properties pertaining to different chemical information from the body. Said reactant material may include but is not limited to ketostix strips, API 20E test strips, nitrocellulose based membranes, glass cellulose-based absorbent pads, pH strips, and the like.

In another embodiment, the bio-sample may be placed into a soluble substance that visually interacts with the bio-sample. Upon successful completion of a bio-sample collection and interaction process, the user is prompted to take an image of the reactive process. The bio-sample image acquisition process may be done within an application from a handheld electronic device, a computer device equipped with a camera, a photographic device, or any other data capture device or system.

Recent research has shown that saliva microbiome profiles are minimally affected by collection methods or DNA extraction protocols which allow bio-sampling of various information derived from the human body. The image data of the bio-sample is uploaded to the server and combined with other data to provide a final dataset.

Figure 4:
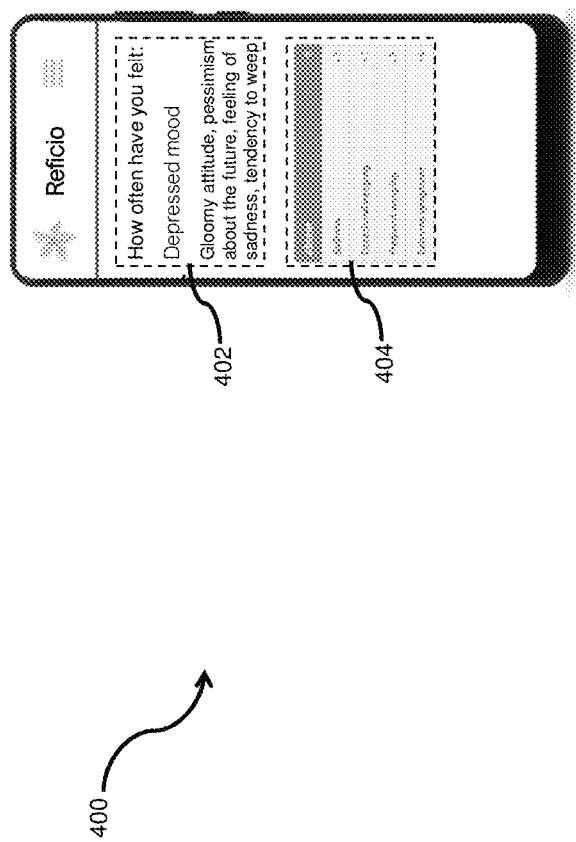
FIG. 4 illustrates a user interface corresponding to a questionnaire module in accordance at least one embodiment of the claimed subject matter.

FIG. 4 illustrates a user interface 400 corresponding to a questionnaire module 212, in accordance with at least one embodiment. FIG. 4 is explained in conjunction with FIG. 2. The memory 112 is configured to receive mental health questionnaire data from the user through a questionnaire module 212. In an embodiment, the questionnaire module presents one or more questions 402 pertaining to the diagnosis of mental health disorders and a plurality of corresponding selectable answers 404. In some embodiments, the questionnaire module facilitates the user to select at least one answer from the plurality of corresponding selectable answers 404 to the one or more questions 402 to obtain the mental health questionnaire data.

According to some embodiments, the user may furthermore be prompted to answer questions pertaining to the state of their mental health. Such questionnaires may include but are not limited to the Goldberg Depression Questionnaire, PHQ-9 Depression Test, Hamilton Depression Rating Scale (HAD-D), Hamilton Anxiety Rating Scale (HAM-A), Generalized Anxiety Disorder Questionnaire-IV, GAD7 Anxiety test questionnaire or other clinical questionnaire process used to assess mental health. Such questionnaires may furthermore include cognitive assessment tests including but not limited to MoCA, MMSE, SLUMS or any other test indicative of cognitive impairment, as well as questionnaires including general questions on the physical state of the user's health.

Figure 5C:
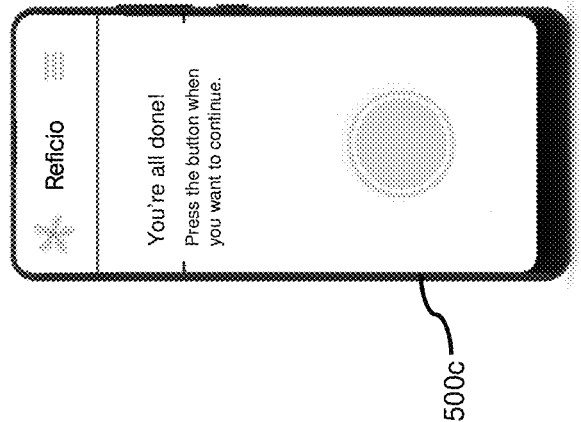
FIGS. 5a-5c illustrate a plurality of user interfaces corresponding to a voice module in accordance at least one embodiment of the claimed subject matter.
Figure 5B:
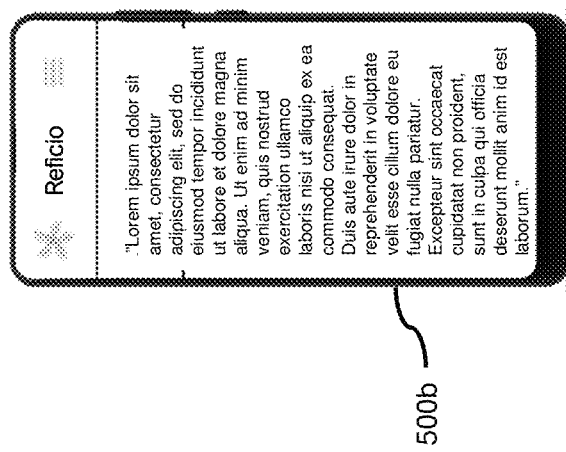
Figure 5A:
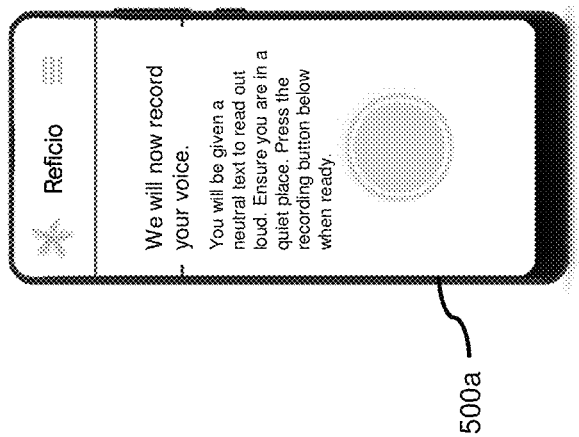

FIGS. 5a-5c illustrate a plurality of user interfaces 500a, 500b, and 500c corresponding to a voice module 206, in accordance with at least one embodiment. FIGS. 5a-5c are explained in conjunction with FIG. 2. The memory 112 is configured to receive voice data of the user through a voice module 206. The user interface 500a depicts an instruction that the voice module 206 will record the voice of the user. The user interface 500b presents textual data to be read by the user. The user interface 500c instructs the user to press a button through a touch gesture after reading the textual data presented on the computing device.

Collection of voice data provides useful insights into establishing more effective management of mental health. It is known that analyzing speech patterns using machine learning methods can be indicative of mental health. Combining such a tool may increase robustness when estimating a mental health disorder progression and can further provide useful insights in addition to a mental health questionnaire. It may also aid in the removal of bias in subsequent mental health order assessment periods. While a patient is typically in control of how they choose to answer on an assessment test and may answer in a way that is not representative of reality, they are typically not aware of slight nuances in their voice patterns that may be indicative of their mental state. It may, therefore, provide a more robust way of measuring mental health as well as heling provide a record of mental health progression over time.

According to an embodiment herein, the voice data is collected in conjunction with the user answering questions related to the user's health. It is well known that machine learning with some degree of accuracy can determine whether a person is providing a false statement or not based on voice analysis. Using machine learning, one may be able to determine if statements regarding the user's health are accurate or not, further enhancing the ability of personalized medicine to be based on accurate information on mental health.

Figure 6B:
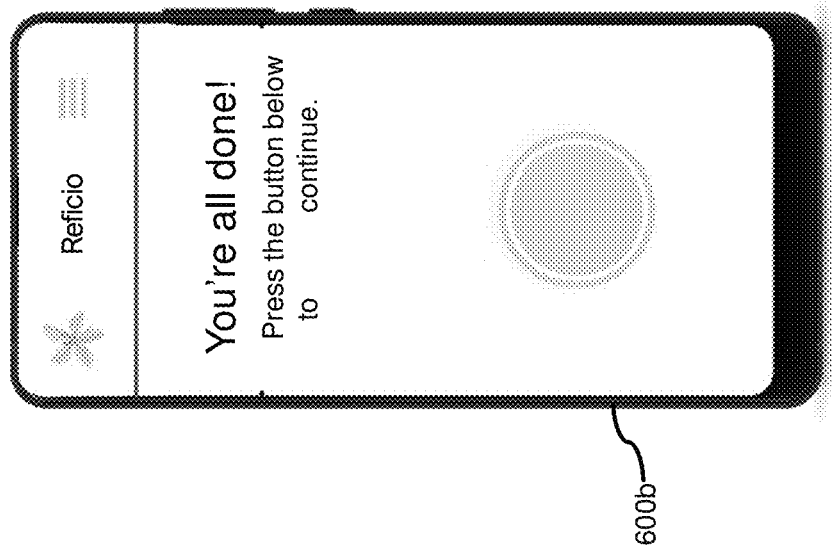
FIGS. 6a-6b illustrate a plurality of user interfaces corresponding to a camera module in accordance at least one embodiment of the claimed subject matter.
Figure 6A:
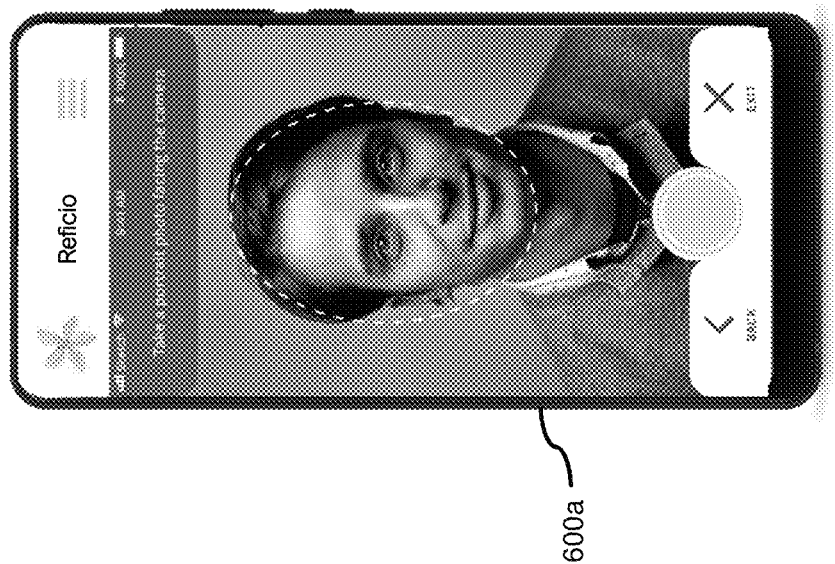

FIGS. 6a-6b illustrate a plurality of user interfaces 600a, and 600b corresponding to a camera module 210, in accordance with at least one embodiment. The memory 112 is configured to receive face image data of the user through a camera module 210. The user interface 600a allows the user to provide the face image of him/her by using the camera of the computing device. The user interface 600b instructs the user to press a button through a touch gesture after providing the face image data presented on the computing device.

According to an embodiment herein, the user is prompted to take one or more pictures of the user's head from one or multiple angles. Such data may be analyzed to determine facial expressions that may be indicative of mental health disorders. It may furthermore be used to identify particular tendencies and characteristics of a person's head and/or face to determine if such is indicative of certain mental health tendencies and/or whether such characteristics are indicative of the efficacy of mental health medicines. It may furthermore serve as an user ID verification process, by correlating said image data of the user's head with a photograph of the user's identification documents, including but not limited to a driver's license, a national identity card and/or passport.

The memory 112 is configured to transmit a final dataset by compiling the demographic data, the voice data, the bio-sample data, the face image data, and the mental health questionnaire data of the user through a data transmission module 214. The server 102 is communicatively coupled to the memory 112 over the network 106. The server 102 is configured to process the final dataset received from the data transmission module 214 by applying a machine learning module 108. The server 102 is configured to generate the tailored medical recipes based on the final dataset processed by the machine learning module 108. The server 102 is configured to transmit the tailored medical recipes to one or more computing devices 104 of the user over the network 106. In an embodiment, the final dataset is uploaded to the server 102 and analysed by various machine learning algorithms associated with the machine learning module 102 to create the tailored medical recipes based on the information submitted by the customer or the user. The medical recipes are medical products produced and shipped directly to the users when complete. Thus, the present computer-implemented method and system provide a diagnostic mechanism as well as supply the medical recipes to the user.

Figure 7:
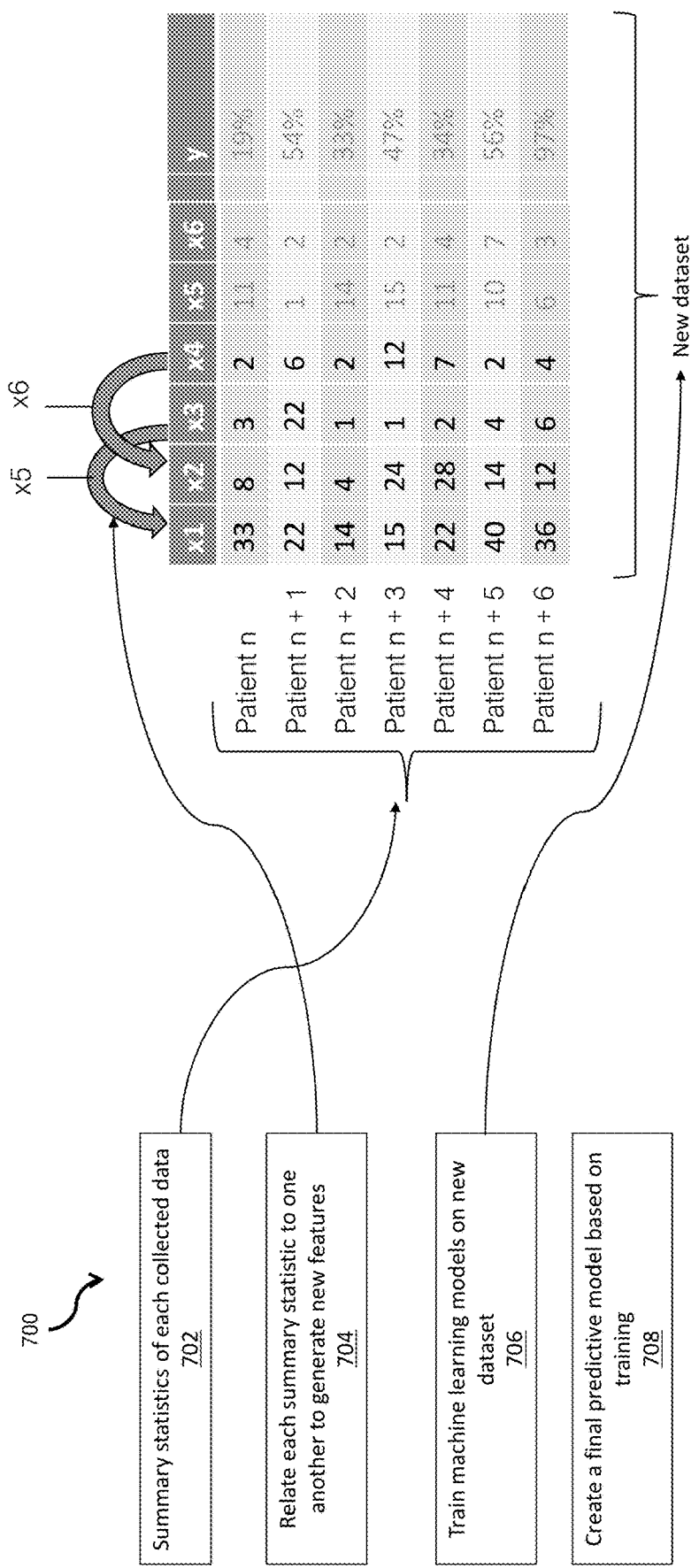
FIG. 7 illustrates a flow diagram of a machine learning training and feature generation through a division of columns by one another in accordance at least one embodiment of the claimed subject matter.

FIG. 7 illustrates a flow diagram 700 of a machine learning training and feature generation through a division of columns by one another, in accordance with at least one embodiment. Block 702 depicts the summary statistics of each collected data. Block step 704 depicts how each summary statistic is related to one another to generate new features. At block 706, machine learning models are trained on a new dataset. At block 708, a final predictive model is created based on training. The Y-variable in the column depicts an absolute level of mental health and/or change in mental health and/or the efficacy of a medical product.

In an embodiment, the machine learning model is trained to predict the effects of certain medicines on mental health progression. Based on the collected data a final dataset may be created by combining the collected data from the user in previous steps with the recipes that were given to the user. This dataset, which may be construed as the 'x-variables', may then be combined with data pertaining to the mental health progression of each patient, this may be construed as the 'y-variable' in the machine learning process. Said mental health progression data of each patient may be collected one or more weeks after the patient has been given their medicine. The machine learning methods may include but are not limited to decision tree-based machine learning methods, artificial neural networks, convolutional neural networks, logistic regression, naive Bayes, nearest neighbor, support vector machines, boosted tree learning methods, and/or generative neural networks.

Figure 8:
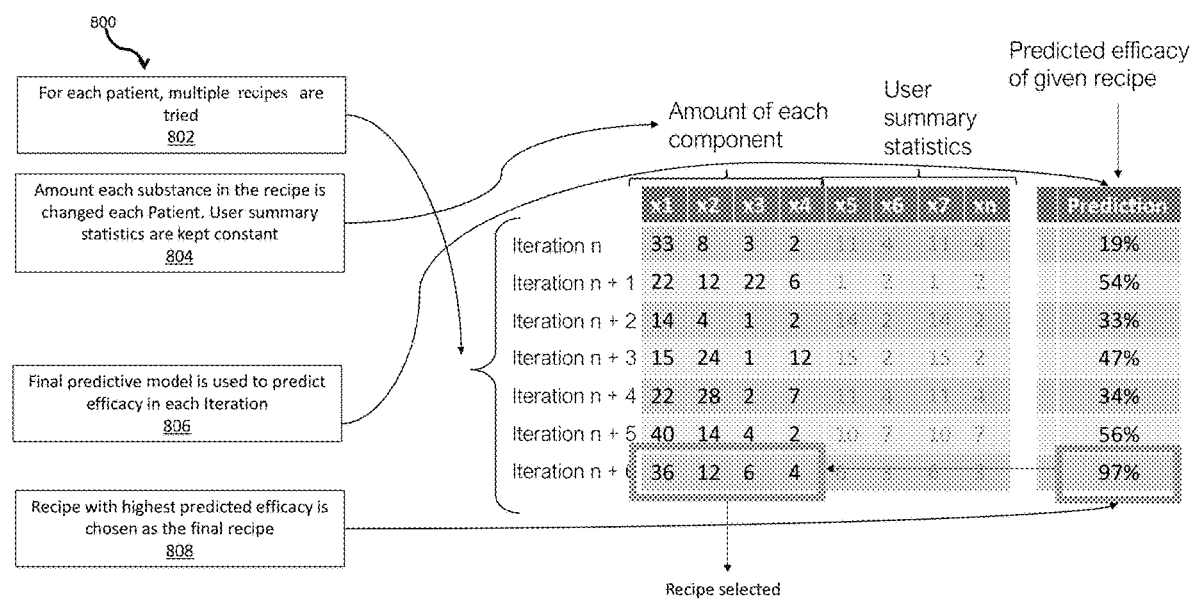
FIG. 8 illustrates a flow diagram of generating the tailored medical recipes in accordance at least one embodiment of the claimed subject matter.

FIG. 8 illustrates a flow diagram 80 of generating the tailored medical recipes, in accordance with at least one embodiment. Block 802 depicts that for each patient, multiple recipes are tried. Block 804 depicts the amount of each substance in the medical recipe is changed for each patient and the user summary statistics are kept constant. At block 806, the final predictive model is used to predict efficacy in each iteration. At block 808, the medical recipe with the highest predicted efficacy is chosen as a final medical recipe for the user.

In an embodiment, for each patient recipes are created and the recipe, or an average of several recipes, with the highest predicted efficacy, may be selected as the final recipe to be produced for the patient.

A solving system may be employed, subject to physical constraints to doses of each variable, to generate a vast number of potential recipes based on the pre-trained model's predicted efficacy as the maximization goal. Such solving systems may include brute force search algorithms and/or may include but are not limited to linear solving methods and/or non-linear solving methods such as genetic algorithm solvers and/or random number generators. In this process, the data collected from the user is held constant, while values for each possible component in the recipe are tailored.

Certain constraints may be imposed on the solving method. Examples of constraints may include total recipe amounts in terms of weight, several different compounds/substances included, for example, a certain minimum or maximum amount per compound that is allowed to be included in the recipe, as well as certain combinations of substances that might be deemed inappropriate.

Substances that may be included in the recipe generation process may include but is not limited to any natural health remedy. It may furthermore include different doses of certified mental health medicines such as selective serotonin reuptake inhibitors (SSRIs), serotonin-norepinephrine reuptake inhibitors (SNRIs), atypical antidepressants such as bupropion (Wellbutrin XL, Wellbutrin SR, Aplenzin, Forfivo XL), mirtazapine (Remeron), nefazodone, trazodone and vortioxetine (Trintellix), tricyclic antidepressants and/or monoamine oxidase inhibitors (MAOIs). It may furthermore include any non-prescription or prescription medicine available known now or in the future.

In an embodiment, a generative adversarial neural networks (GANs) approach may be employed to generate potential recipes based on the data submitted by the user. Such GANs may include Deep Convolutional GANs (DC-GANs), Wasserstein GANs (WGANs), Self-Attention GANs (SAGANs), and BigGANs. Variational autoencoders may furthermore be used in the training process. Such methods may be useful in overcoming the overfitting of the data.

In some embodiments, one or more specific diets may be recommended to the user as a way of improving the user's wellbeing and health. Diet is a well-known variable known to be a factor in mental health, physical health and general wellbeing.

In some embodiments, natural medicine and/or recipes pertaining to cardiac health including but not limited to hypertension and heart failure may be tailored to the user. It is well known that cardiac chronic conditions such as hypertension may experience many negative emotions which increase their risk for the development of mental health disorders particularly anxiety and depression. In many of these embodiments, a final dataset may further be comprised of data pertaining to measuring the absolute level of hemodynamic and/or intracardiac pressure and/or other clinical cardiac measurements in the patient measured by one or more invasive and/or non-invasive products.

In some embodiments, natural medicine, blends and/or recipes having anticoagulating properties may be tailored to the user. It is known that mental stress affects coagulation, while severe mental illnesses, including depression, are associated with an increased thrombotic risk and cardiovascular morbidity. In such an embodiment, a final dataset may further be comprised of data pertaining to measuring the degree of thrombosis progression in the patient measured by ultrasound, D-dimer test and/or other non-invasive devices comprising microphonic and/or inertial measurement unit sensors.

In many of the described embodiments, follow up information from the user may be collected which can aid in the analysis of the metadata associated with the predicted recipes. In some embodiments, future variations of the one or more recipes may be created and comparisons of how well the predicted recipes performed with real data may be used to adjust other predictions. Using this data, many of these embodiments can use machine learning models to create additional blends and recipes.

In some embodiments, the software application may provide an option of connecting via voice and/or video interaction and/or offering psychotherapeutic methods including but not limited to cognitive behavioral therapy, psychoanalysis and psychosynthesis to the user. In many of these embodiments, such communication may be performed through an automated response system driven by artificial intelligence including examples such as chatbots and the like.

Figure 9:
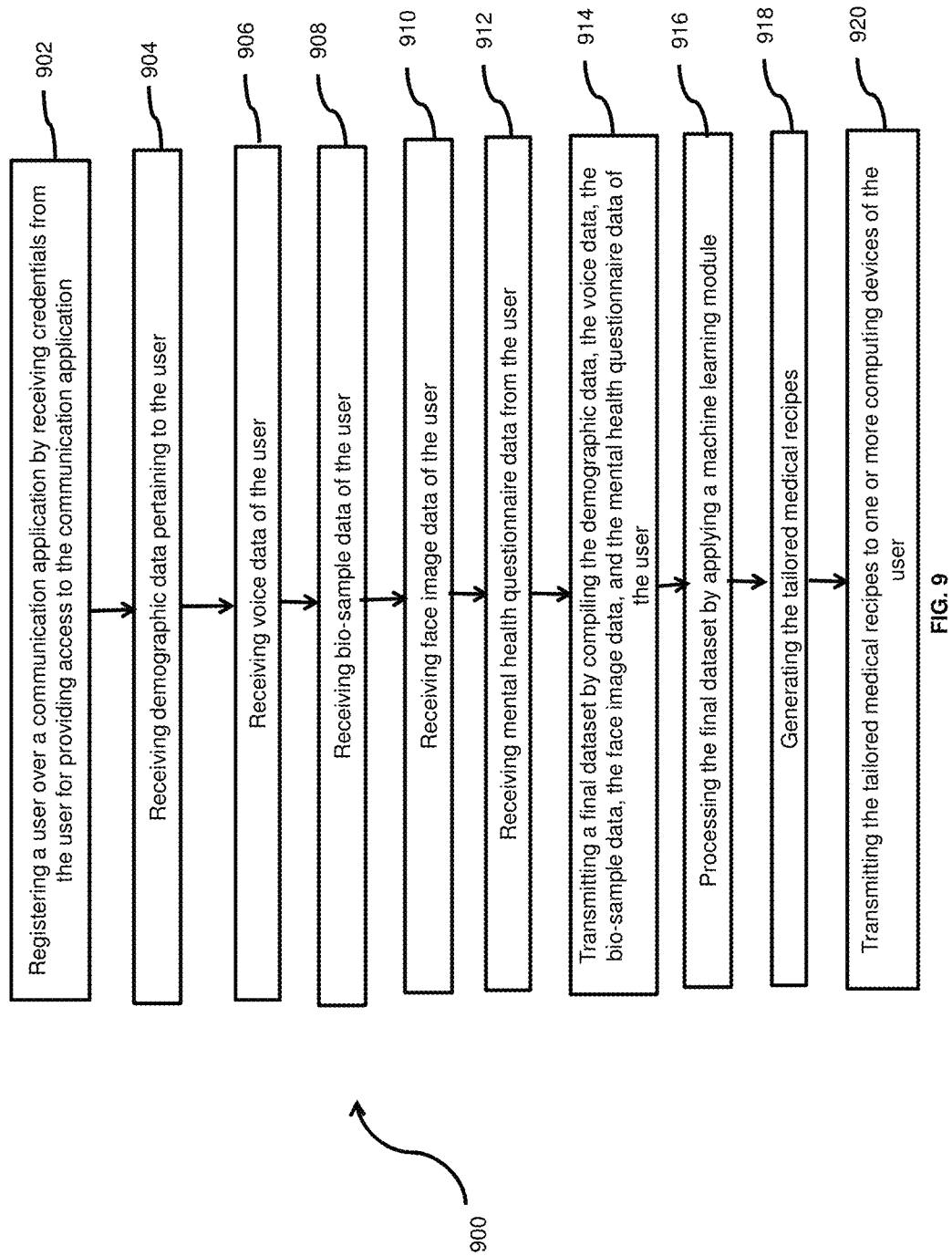
FIG. 9 illustrates a flowchart of the computer-implemented method for generating one or more tailored medical recipes for mental health disorders in accordance at least one embodiment of the claimed subject matter.

FIG. 9 illustrates a flowchart 900 of the computer-implemented method for generating one or more tailored medical recipes for mental health disorders, in accordance with embodiments of the inventive subject matter. The computer-implemented method includes a step 902 of registering a user over a communication application by receiving one or more credentials from the user for providing access to the communication application through a registration module. In this embodiment, the communication application is executable on the computing devices of the user which is implemented on one or more operating systems. The computer-implemented method includes a step 904 of receiving demographic data pertaining to the user through a demography module. The computer-implemented method includes a step 906 of receiving voice data of the user through a voice module.

The computer-implemented method includes a step 908 of receiving bio-sample data of the user through a bio-sample module. In these embodiments, the bio-sample module is configured to facilitate the user to collect a bio-sample from salivary glands in a form of saliva. In these embodiments, the bio-sample module is configured to facilitate the user to place the bio-sample on a reactant paper comprising one or more reactant properties pertaining to chemical information of the user's body. In some embodiments, the bio-sample module is configured to facilitate the user to capture an image of the reactant paper upon placing the bio-sample to obtain the bio-sample data.

The computer-implemented method includes a step 910 of receiving face image data of the user through a camera module. The computer-implemented method includes a step 912 of receiving mental health questionnaire data from the user through a questionnaire module. In some embodiments, the questionnaire module presents one or more questions pertaining to the diagnosis of mental health disorders and a plurality of corresponding selectable answers. In some embodiments, the questionnaire module facilitates the user to select at least one answer from the plurality of corresponding selectable answers to the one or more questions to obtain the mental health questionnaire data.

The computer-implemented method includes a step 914 of transmitting a final dataset by compiling the demographic data, the voice data, the bio-sample data, the face image data, and the mental health questionnaire data of the user through a data transmission module. The computer-implemented method includes a step 916 of processing the final dataset received from the data transmission module over a network by applying a machine learning module. The computer-implemented method includes a step 918 of generating the tailored medical recipes based on the final dataset processed by the machine learning module. The computer-implemented method includes a step 920 of transmitting the tailored medical recipes to one or more computing devices of the user.

Embodiments of the present computer-implemented systems and methods can be extended to other mental health and/or cognitive related diseases including, but not limited to, dementia and Alzheimer's disease. A personalized medicine approach is taken to a disease such as dementia. It is well-known that particular voice patterns, facial patterns may be related to mild cognitive impairment and possibly biomarkers associated with dementia. In such an embodiment, retina analysis, for example with the aid of the camera, may be an important part of the present embodiments. It is known that serotonin levels may be correlated with general mental health or even with levels of dementia. It has also recently been documented that there are significant differences in gut microbiome levels between dementia and non-dementia patients. Oral microflora may also be able to influence brain functions. The collection of data using the described embodiments may therefore provide additional insights into tailored medical recipe generation for mental health diseases such as dementia and/or other neurodegenerative diseases.

Embodiments of the present computer-implemented systems and methods utilize a software application configured within the computer device of the user includes a camera to enable the user to capture one or multiple images of the bio-sample through a visual reaction with a reactant material. Further, the software application collects voice audio data and/or the collection of mental health assessment questionnaire data and/or demographic data of the user. In many embodiments, the software application prompts the user to take one or multiple photos of the bio-sample. The user also submits additional data pertaining to voice audio and/or mental health assessment questionnaire and/or demographic data. Then the software application generates one or multiple datasets and analyses this data on the computing device or transmits it to a server for analysis using machine learning methods. Based on features uncovered from the dataset, estimating the likelihood of a mental health disorder and/or the severity of a mental health disorder, inputting said estimations with the collected data to generate a new dataset. Correlating said new dataset with compositions of substances related to declines in mental health disorders to generate one or more tailored medical recipes based on said user's characteristics.

Unless otherwise defined, all terms (including technical and scientific terms) used in this disclosure have the same meaning as commonly understood by one of ordinary skill in the art. It is to be understood that the phrases or terms employed in the instant disclosure are for description and are not limited in any way. As will be appreciated by one skilled in the art, the present disclosure may be embodied as one or more apparatus, device, system, method and/or computer program. Further, the inventive subject matter may take the form of a computer program product on a computer-readable storage medium having computer-usable program code embodied in the medium. The present systems and methods have been described above with reference to specific examples as illustrations of the inventive subject matter.

However, a number of other embodiments are also possible and within the scope of the present inventive subject matter. Even though modifications and changes may be suggested by the persons skilled in the art, it is the intention of the inventors and applicants to embody within the patent warranted heron all the changes and modifications as reasonably and properly come within the scope of the claimed subject matter.

What is claimed is:

1. A computer-implemented method for generating one or more tailored medical recipes for mental health disorders, the computer-implemented method comprising:

registering, by one or more processors, a user over a communication application by receiving one or more credentials from the user for providing access to the communication application through a registration module;

receiving, by the one or more processors, demographic data pertaining to the user through a demography module;

receiving, by the one or more processors, bio-sample data of the user through at least one bio-sample module;

receiving, by the one or more processors, mental health questionnaire data from the user through a questionnaire module;

transmitting, by the one or more processors, a final dataset by compiling the demographic data, the bio-sample data, and the mental health questionnaire data of the user through a data transmission module;

processing, by a server, the final dataset received from the data transmission module over a network by applying a machine learning module;

generating, by the server, the tailored medical recipes based on the final dataset processed by the machine learning module, wherein the server generates the tailored medical recipes for treatment or diagnostic or prevention of mental health disorders, or any combination of treatment or diagnostic or prevention of mental health disorders based on the final dataset processed by the machine learning module; and transmitting, by the server, the tailored medical recipes to one or more computing devices of the user, wherein the machine learning module is configured to generate features from the final dataset to estimate at least one of a likelihood of a future occurrence of the mental health disorder and severity of the mental health disorder or both, wherein the machine learning module is configured to generate a new dataset based on a combination of the final dataset and the estimations of the at least one of a likelihood of a future occurrence of the mental health disorder and severity of the mental health disorder or both, wherein the machine learning module is configured to correlate the new dataset with one or more compositions of the tailored medical recipes related to declining in the mental health of the user to generate another one or more tailored medical recipes different from the tailored medical recipes generated from the final dataset processed by the machine learning module, wherein the machine learning module is trained to predict effects of the tailored medical recipes on progression of the mental health of the user, wherein the server employs a generative adversarial neural network (GAN) to generate the tailored medical recipes based on the user's data, wherein the GAN comprising one or more Deep Convolutional GANs (DCGANs), one or more Wasserstein GANs (WGANs), and one or more Self-Attention GANs (SAGANs).

2. The computer-implemented method of claim 1, wherein the bio-sample module is configured to facilitate the user to collect a bio-sample from salivary glands in a form of saliva.

3. The computer-implemented method of claim 1, wherein the bio-sample module is configured to facilitate the user to place the bio-sample on a reactant paper having one or more reactant properties pertaining to chemical information of the user's body.

4. The computer-implemented method of claim 1, wherein the bio-sample module is configured to facilitate the user to capture an image of the reactant paper upon placing the bio-sample to obtain the bio-sample data.

5. The computer-implemented method of claim 1, wherein the questionnaire module facilitates the user to select at least one answer from the plurality of corresponding one or more selectable answers to the one or more questions in order to obtain mental health questionnaire data.

6. The computer-implemented method of claim 1, wherein a user's voice data is received through a voice module and processed by the one or more processors, wherein transmitting, by the one or more processors, a final dataset by compiling the demographic data, the bio-sample data, and the mental health questionnaire data of the user through a data transmission module includes compiling the user's voice data.

7. The computer-implemented method of claim 1, wherein the user's face image data is received though a camera module and processed by the one or more processors, wherein transmitting, by the one or more processors, a final dataset by compiling the demographic data, the bio-sample data, and the mental health questionnaire data of the user through a data transmission module includes compiling the user's face image data.

8. The computer-implemented method of claim 1, wherein the server generates one or more tailored diets based on the final dataset processed by the machine learning module.

9. The computer-implemented method of claim 1, wherein the server generates one or more tailored medical recipes pertaining to cardiac health based on the final dataset processed by the machine learning module.

10. The computer-implemented method of claim 1, wherein the server generates one or more tailored medical recipes having anticoagulating properties based on the final dataset processed by the machine learning module.

11. The computer-implemented method of claim 1, wherein the server generates one or more tailored medical recipes for the treatment and/or prevention of dementia based on the final dataset processed by the machine learning module.

12. A system for generating one or more tailored medical recipes for mental health disorders, the system comprising:
a processor;
a memory communicatively coupled to the processor, wherein the memory stores instructions executed by the processor, wherein the memory is configured to:
register a user over a communication application by receiving one or more credentials from the user for providing access to the communication application through a registration module;
receive demographic data pertaining to the user through a demography module;
receive bio-sample data of the user through a bio-sample module;
receive mental health questionnaire data from the user through a questionnaire module; and
transmit a final dataset by compiling the demographic data, the bio-sample data, and the mental health questionnaire data of the user through a data transmission module; and
a server communicatively coupled to the memory over a network, wherein the server is configured to:
process the final dataset received from the data transmission module by applying a machine learning module;
generate the tailored medical recipes based on the final dataset processed by the machine learning module, wherein the server generates the tailored medical recipes for treatment or diagnostic or prevention of mental health disorders, or any combination of treatment or diagnostic or prevention of mental health disorders based on the final dataset processed by the machine learning module; and
transmit the tailored medical recipes to one or more computing devices of the user over the network, wherein the machine learning module is configured to generate features from the final dataset to estimate at least one of a likelihood of a future occurrence of the mental health disorder and severity of the mental health disorder or both, wherein the machine learning module is configured to generate a new dataset based on a combination of the final dataset and the estimations of the at least one of a likelihood of a future occurrence of the mental health disorder and severity of the mental health disorder or both, wherein the machine learning module is configured to correlate the new dataset with one or more compositions of the tailored medical recipes related to declining in the mental health of the user to generate another one or more tailored medical recipes different from the tailored medical recipes generated from the final dataset processed by the machine learning module, wherein the machine learning module is trained to predict effects of the tailored medical recipes on progression of the mental health of the user, wherein the server employs a generative adversarial neural network (GAN) to generate the tailored medical recipes based on the user's data, wherein the GAN comprising one or more Deep Convolutional GANs (DCGANs), one or more Wasserstein GANs (WGANs), and one or more Self-Attention GANs (SAGANs).

13. The system of claim 12, wherein the bio-sample module samples saliva.

14. The system of claim 12, wherein the bio-sample module is configured to facilitate the user to place the bio-sample on a reactant paper comprising a plurality of reactant properties pertaining to chemical information of the user's body.

15. The system of claim 12, wherein the bio-sample module is configured to facilitate the user to capture an image of the reactant paper upon placing the bio-sample to obtain the bio-sample data.

16. The system of claim 12, wherein the questionnaire module presents one or more questions pertaining to diagnosis of mental health disorders and a plurality of corresponding selectable answers.

17. The system of claim 12, wherein the questionnaire module facilitates the user to select at least one answer from the plurality of corresponding selectable answers to the one or more questions to obtain the mental health questionnaire data.

18. The system of claim 12, wherein the system receives voice data of the user through a voice module, wherein the memory is configured to transmit, by the one or more processors, the final dataset by compiling the demographic data, the bio-sample data, the mental health questionnaire data of the user, and the user's voice data through a data transmission module.

19. The system of claim 12, wherein the system receives face image data of the user through a camera module, wherein the memory is configured to transmit, by the one or more processors, the final dataset by compiling the demographic data, the bio-sample data, the mental health questionnaire data of the user, and the face image data of the user through a data transmission module.

20. The system of claim 12, wherein the server is configured to generate one or more tailored diets to the user based on the final dataset processed by the machine learning module.

21. The system of claim 12, wherein the server is configured to generate one or more tailored medical recipes pertaining to cardiac health based on the final dataset processed by the machine learning module.

22. The system of claim 12, wherein the server is configured to generate one or more tailored medical recipes having anticoagulating properties based on the final dataset processed by the machine learning module.

23. The system of claim 12, wherein the server is configured to generate one or more tailored medical recipes for treatment and/or prevention of dementia based on the final dataset processed by the machine learning module.

24. A non-transitory computer-readable storage medium storing executable instructions for generating one or more tailored medical recipes for mental health disorders that, as a result of being executed by one or more processors of a computer system, cause the computer system to at least:

register a user over a communication application by receiving one or more credentials from the user for providing access to the communication application through a registration module;

receive demographic data pertaining to the user through a demography module;

receive bio-sample data of the user through a bio-sample module;

receive mental health questionnaire data from the user through a questionnaire module;

transmit a final dataset by compiling the demographic data, the bio-sample data, and the mental health questionnaire data of the user through a data transmission module;

process the final dataset received from the data transmission module by applying a machine learning module;

generate the tailored medical recipes based on the final dataset processed by the machine learning module, wherein the server generates the tailored medical recipes for treatment or diagnostic or prevention of mental health disorders, or any combination of treatment or diagnostic or prevention of mental health disorders based on the final dataset processed by the machine learning module; and transmit the tailored medical recipes to one or more computing devices of the user over the network, wherein the machine learning module is configured to generate features from the final dataset to estimate at least one of a likelihood of a future occurrence of the mental health disorder and severity of the mental health disorder or both, wherein the machine learning module is configured to generate a new dataset based on a combination of the final dataset and the estimations of the at least one of a likelihood of a future occurrence of the mental health disorder and severity of the mental health disorder or both, wherein the machine learning module is configured to correlate the new dataset with one or more compositions of the tailored medical recipes related to declining in the mental health of the user to generate another one or more tailored medical recipes different from the tailored medical recipes generated from the final dataset processed by the machine learning module, wherein the machine learning module is trained to predict effects of the tailored medical recipes on progression of the mental health of the user, wherein the server employs a generative adversarial neural network (GAN) to generate the tailored medical recipes based on the user's data, wherein the GAN comprising one or more Deep Convolutional GANs (DCGANs), one or more Wasserstein GANs (WGANs), and one or more Self-Attention GANs (SAGANs).

* * * * *